Figure 1:
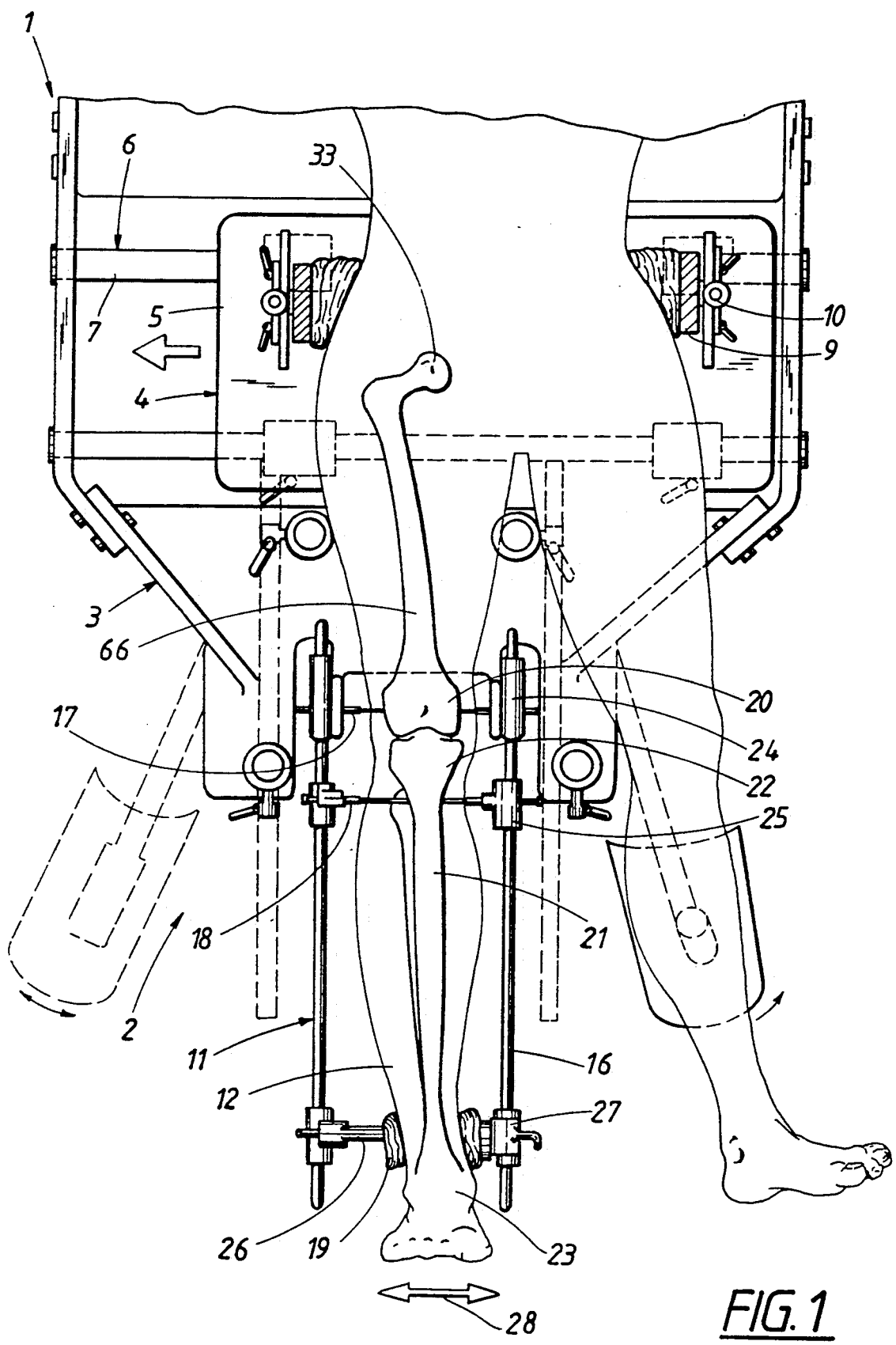

United States Patent [19]
Albrektsson et al.

[11] Patent Number: 5,007,912
[45] Date of Patent: Apr. 16, 1991

[54] ARRANGEMENT FOR FIXING A KNEE-JOINT IN DEFINED POSITIONS AND FOR POSITIONAL CONTROL OF INSTRUMENTS FOR REPLACING THE KNEE-JOINT WITH A PROSTHESIS

[76] Inventors: Björn Albrektsson, Värslevägen 39, Askim, Sweden, S-436 43; Stig Wennberg, Villa Holma Pl 6266, Angered, Sweden, S-424 57

[21] Appl. No.: 530,611

[22] Filed: May 30, 1990

[51] Int. Cl.$^5$ .......................... A61F 5/04; A61F 5/37; A61G 13/00
[52] U.S. Cl. ........................................ 606/87; 606/88; 128/882; 269/322
[58] Field of Search ............. 128/870, 877, 882, 84 R, 128/84 C; 606/86, 87, 88, 53, 54, 55; 269/322, 323, 324, 325

[56] References Cited

U.S. PATENT DOCUMENTS

| | | | |
|---|---|---|---|
| 2,057,992 | 10/1936 | Wiruth | 128/84 R |
| 3,625,210 | 12/1971 | Mikkelson | 128/877 |
| 4,299,213 | 11/1981 | Violet | 128/882 |
| 4,373,709 | 2/1983 | Whitt | 128/882 |
| 4,407,277 | 10/1983 | Ellison | 128/882 |
| 4,457,302 | 7/1984 | Caspari | 128/882 |
| 4,549,540 | 10/1985 | Caspari | 128/882 |

Primary Examiner—Robert A. Hafer
Assistant Examiner—Michael Brown
Attorney, Agent, or Firm—Lerner, David, Littenberg, Krumholz & Mentlik

[57] ABSTRACT

The invention relates to an arrangement for fixing a knee-joint in connection with prosthetic surgery. The arrangement provides for a fixing of the operated knee-joint relative to a reference, which is represented by the operating table. The purpose is to positionally control, with high precision, measuring and cutting instruments in the prosthesis operation. The arrangement includes an alignment instrument (11) for aligning and fixing both the femur (66) and tibia (21) relative to a reference axis in both the frontal plane and the sagittal plane, which alignment instrument comprises a fixture (4) for the trunk. The fixture is adjustable and can be locked in selected positions by displacement transverse to the reference axis. The alignment instrument also comprises a further fixture for fixing the knee-joint (20, 22) and tibia (21). The arrangement moreover comprises a positional control unit for positional control of measuring and cutting instruments. This permits a controlled, precise and delicate bone-cutting, which creates the conditions for the desired positioning and exact fitting between prosthesis bed and prosthesis.

9 Claims, 7 Drawing Sheets

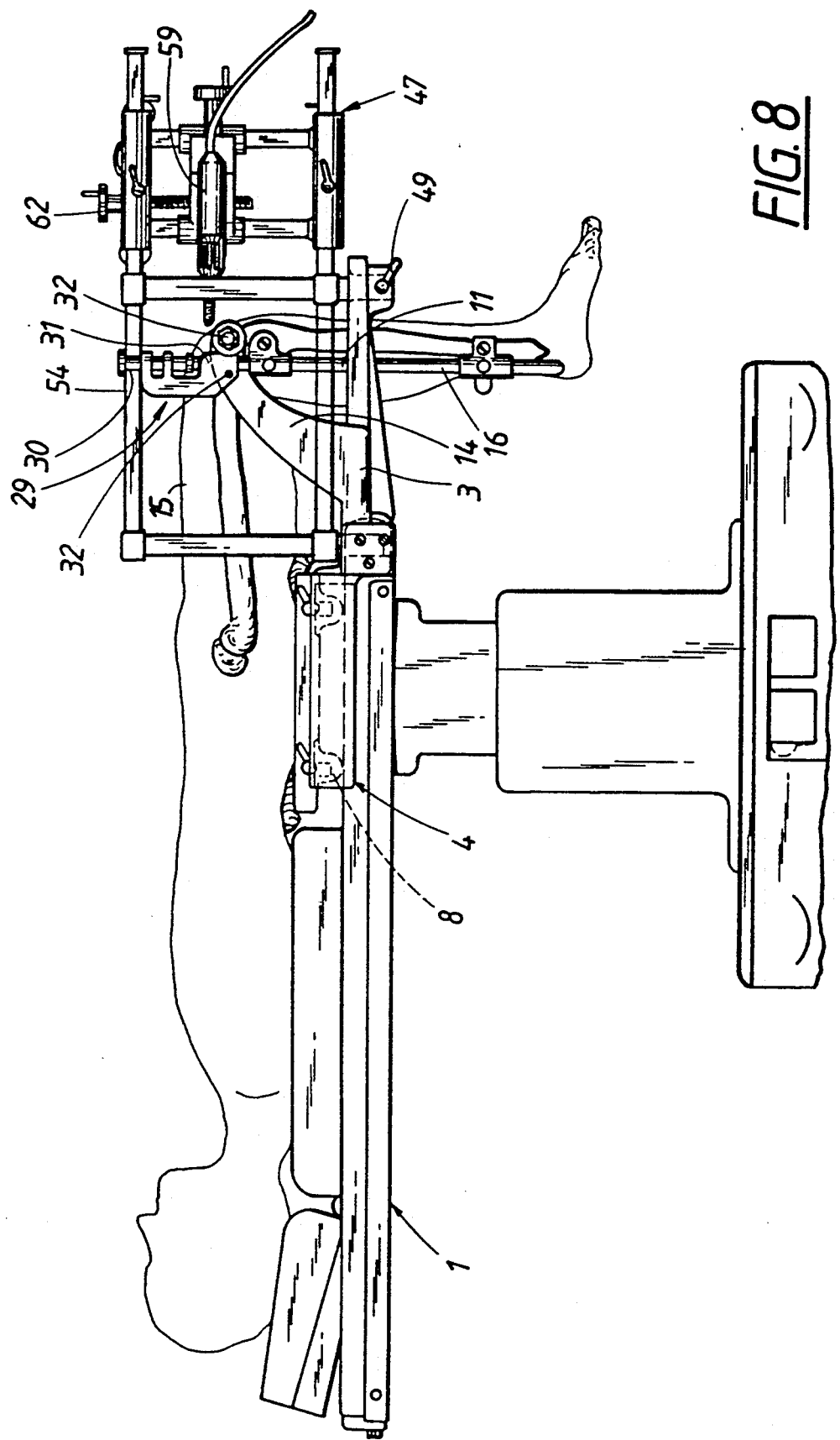

ARRANGEMENT FOR FIXING A KNEE-JOINT IN DEFINED POSITIONS AND FOR POSITIONAL CONTROL OF INSTRUMENTS FOR REPLACING THE KNEE-JOINT WITH A PROSTHESIS

TECHNICAL FIELD

The present invention relates to an arrangement for fixing a knee-joint in defined positions and for positional control of instruments for replacing the kneejoint of a patient with a prosthesis, which arrangement is designed to be connected to an operating table intended to support the patient.

TECHNICAL PROBLEM

In connection with the implantation of knee-joint prostheses in knee-joints for prosthetic surgery of the knee, relatively primative means are used for fixing the kneejoint and for positional control of the surgical instrument. Previously known arrangements involve very inexact cutting of those parts which are to be removed in the operation. Furthermore, in many cases the operating time is unfavourably long and results in high heat production, with the risk of the patient suffering traumatic effects. A very important disadvantage with the known arrangements is that the poor precision in cutting of the bone tissue results in an inexact fitting between prosthesis and bone, which can jeopardize the anchoring of the prosthesis. The previously known technology has mainly been used for knee-joint replacements in patients with low activity, such as persons older than about 60 years of age. Even in these cases, knee-joint replacement has involved a limited prosthesis life.

The aim of the present invention is to provide a technique for exact atraumatic cutting of bone ends constituting a seat for the knee prosthesis which, by means of the arrangement, can be placed in the desired position

SOLUTION

The said aim is achieved by means of an arrangement according to the present invention, which is characterized in that the arrangement comprises, on the one hand, a stand which can be connected to the operating table, an alignment instrument which is supported by the stand and is used for aligning both the femur and tibia relative to a reference axis, and, on the other hand, a positional control unit which can be connected to the stand in defined positions and is used for positional control of at least one instrument relative to the kneejoint, which alignment instrument comprises a fixture, supported by the stand, for the trunk of the patient, which trunk fixture is adjustable and can be locked in selected positions by displacement transverse to the said reference axis, and a limb fixture, supported by the stand, for fixing the knee-joint and ankle-joint of the patient, in that the said limb fixture for fixing the knee-joint and ankle-joint consists of a fixation frame which is pivotably mounted on the stand by means of a pivot hinge and which, by means of its pivotability, can be set in different angular positions relative to the operating table.

Figure 2:
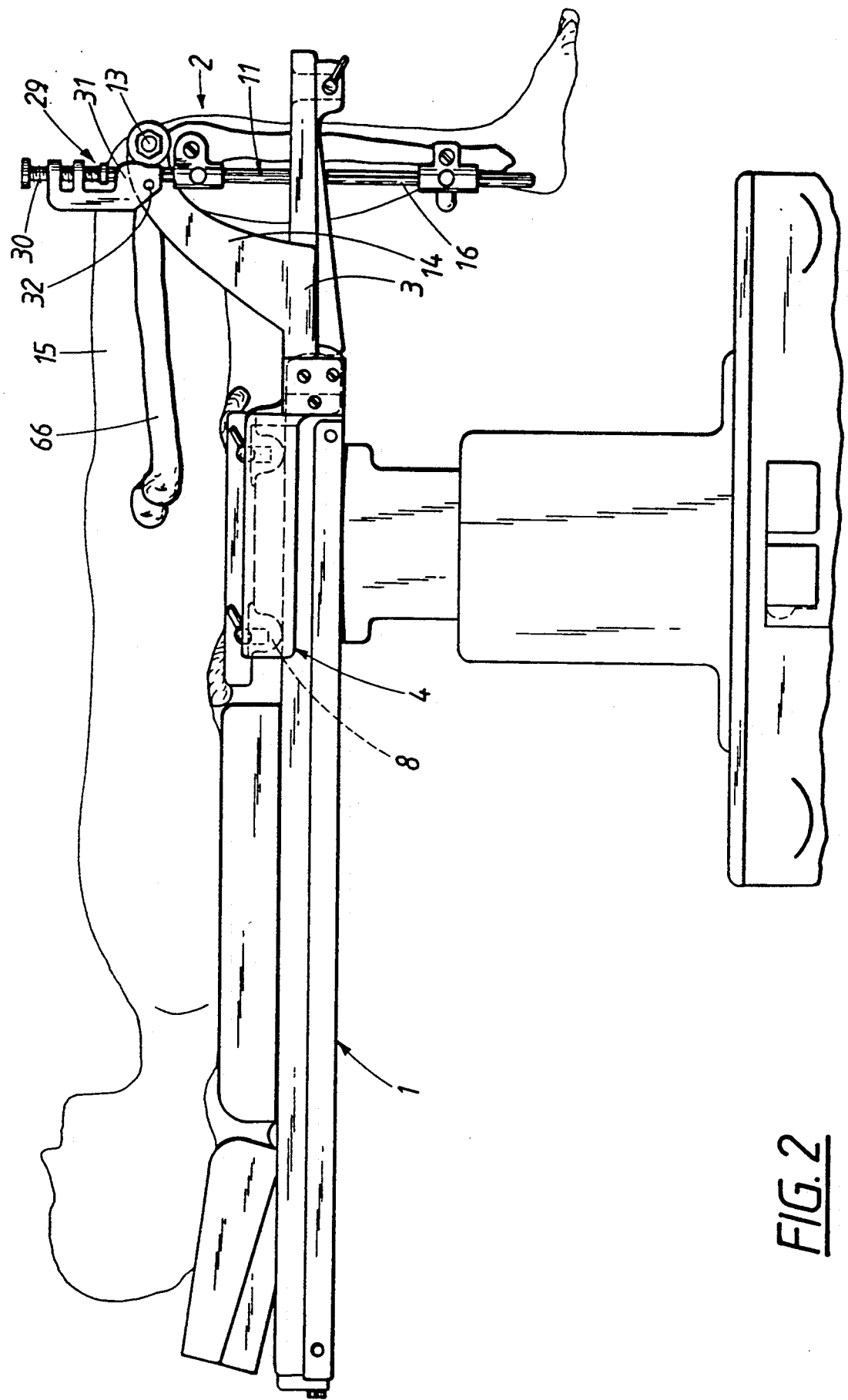
Figure 3:
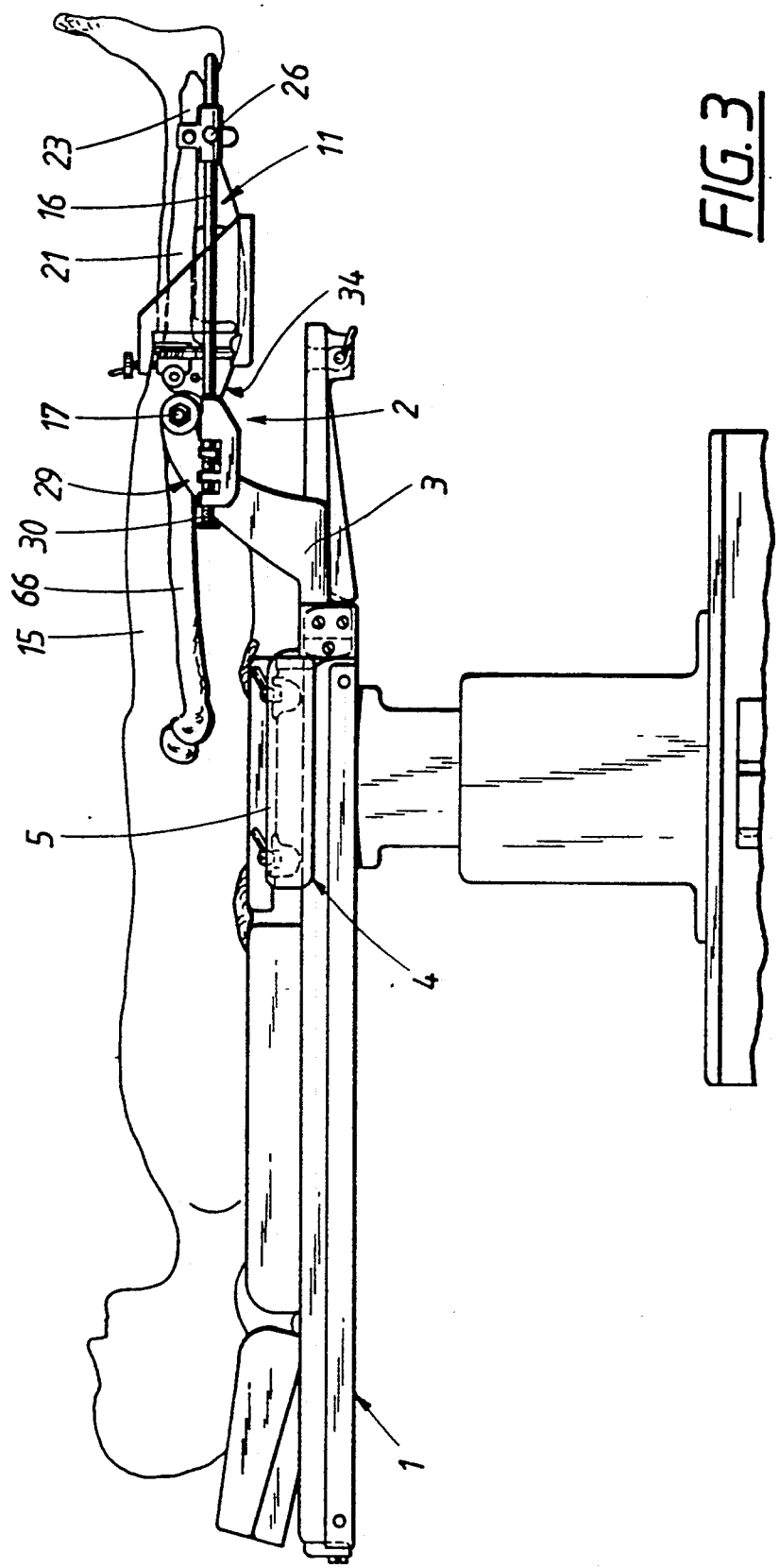
Figure 4:
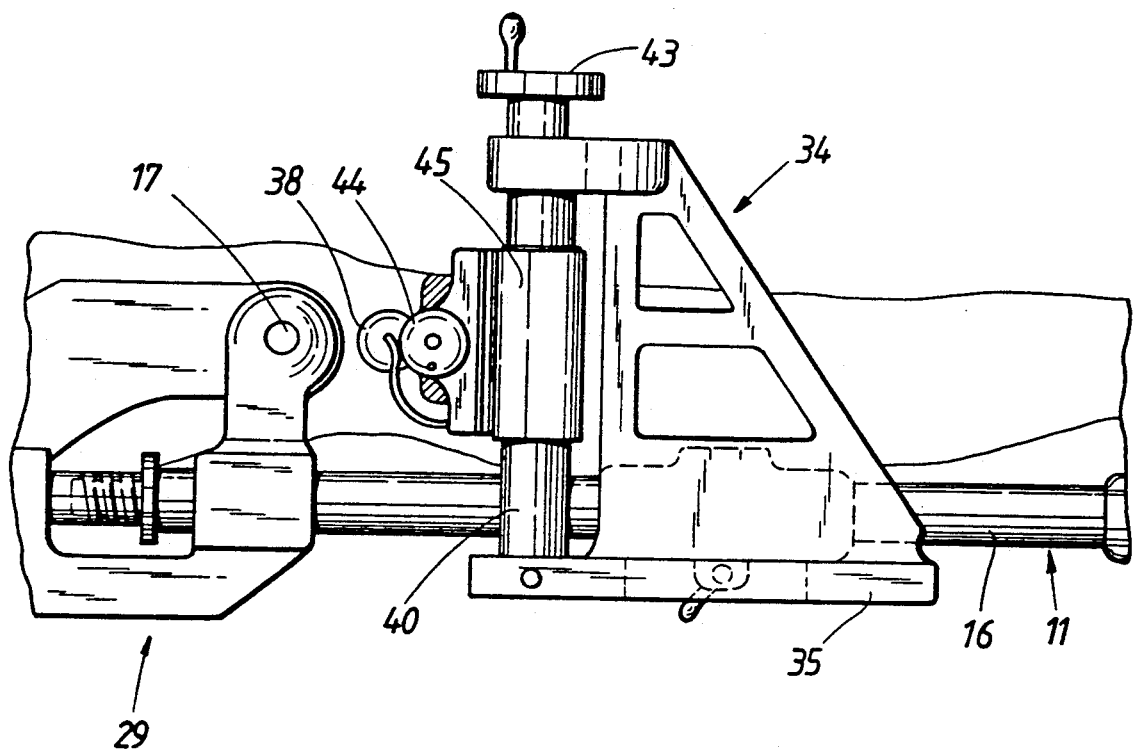
Figure 5:
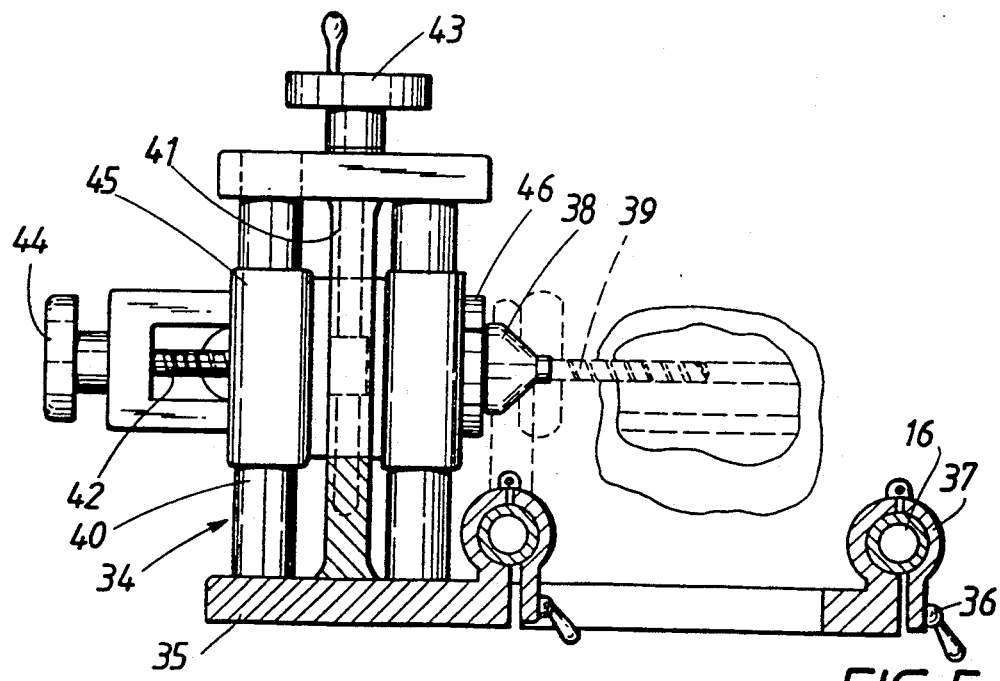

The invention will be illustrated in greater detail below on the basis of an exemplary embodiment and with reference to the attached drawings, in which FIG. 1 shows a plan view of an alignment instrument incorporated in the arrangement according to the invention, FIG. 2 shows the alignment instrument set in an operating position, FIG. 3 shows the arrangement with the alignment instrument and a cutting and assembly tool connected to it, while FIGS. 4 and 5 show two different views of the cutting and assembly tool on a larger scale.

Figure 6:
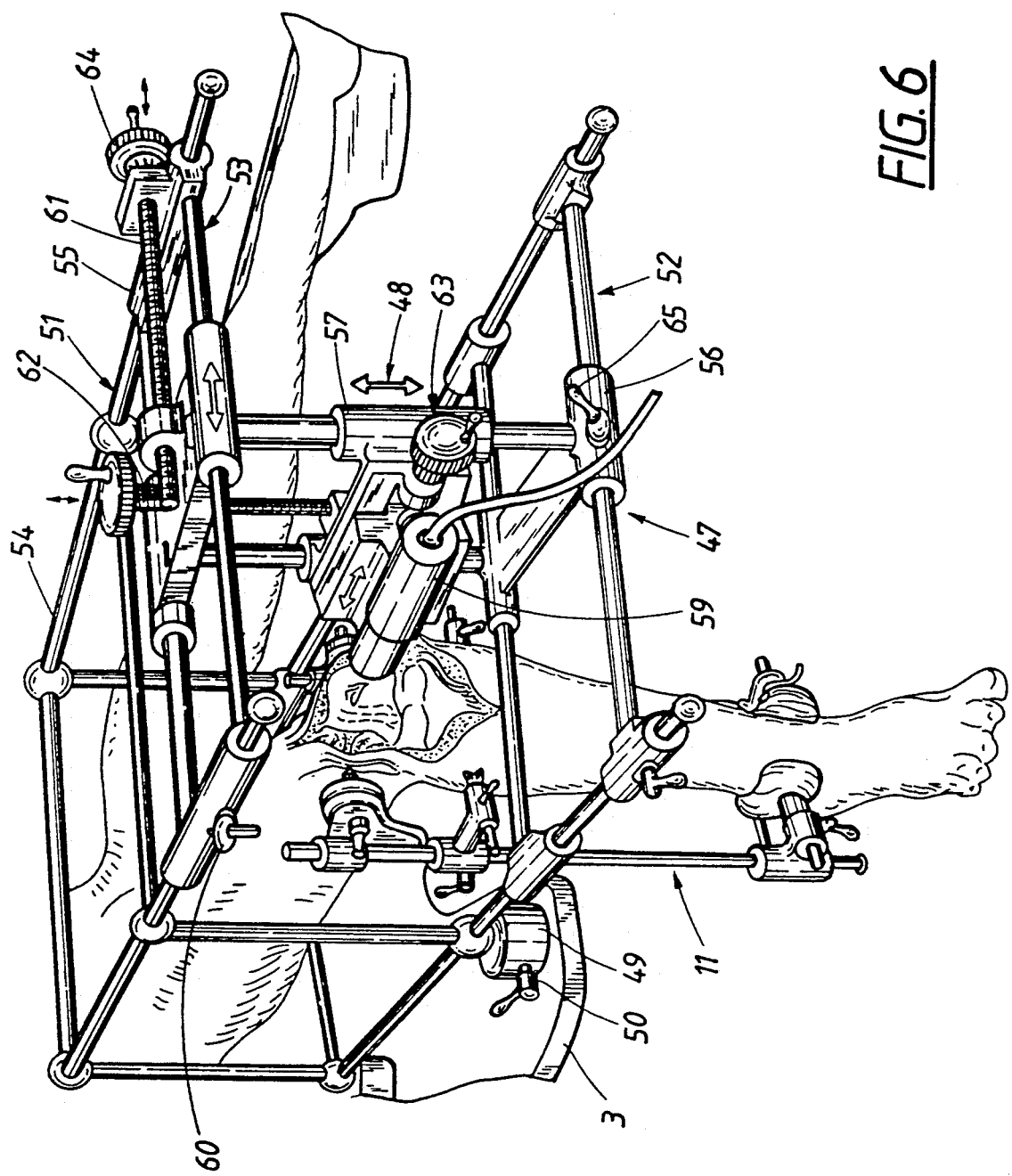
Figure 7:
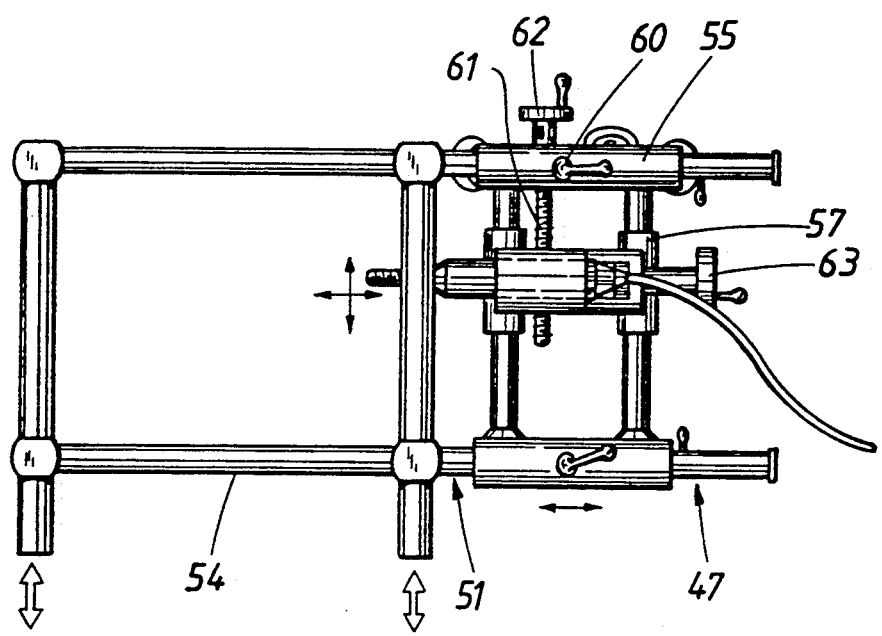

FIG. 6 shows a perspective view of the alignment instrument supplemented with a positional control unit for a second cutting instrument according to the invention, FIG. 7 shows a separate side view of the positional control unit with the said cutting instrument, and FIG. 8 shows a side view of an operating table with the patient, and with the arrangement according to the invention in operation.

The arrangement according to the invention forms a unit which can be integrated with a conventional operating table 1, as is shown, for example, in FIGS. 1 and 2. The arrangement can either be designed as a separate additional element, which can be assembled subsequently on existing operating tables, or can from the start be integrated with operating tables specially designed for the type of surgical intervention in question, which in this case is knee-joint replacement. The arrangement according to the invention comprises an alignment instrument 2 and a stand 3, fixed at the bottom end of the operating table, in which respect the alignment instrument has a fixture 4 for the trunk of the patient. As emerges most clearly from FIG. 1, the fixture 4 comprises a slide 5 which can be displaced relative to the stand 3 transverse to the longitudinal direction of the patient. The displacement movement is made possible by means of a guide arrangement 6 which, in the example shown, is made up of two parallel bars 7, which are at least partially surrounded by runner members 8 connected to the slide 5. By means of a locking arrangement in connection with at least one of the runner members, the slide 5 can be locked in a chosen lateral displacement position. This locking arrangement can be of a type conventional per se, for example with clamping members which lock against the associated rod with frictional locking. The slide 5 has two padded hip-positioning members 9 which, by means of an adjustable attachment 10, can be adjusted so as to vary the space between the positioning members 9 between different positions in the longitudinal direction of the patient. The attachments 10 are moreover designed so that they automatically take up an angular position adapted to the contour of the patient. The arrangement described thus forms an adjustable fixture 4 for the trunk or hipbones of the patient, which parts of the body can therefore be moved sideways and fixed in a defined position.

The alignment instrument 2 furthermore comprises an adjustable limb fixture 11. For the sake of simplicity, this fixture will be referred to from now on as the leg fixture 11. The leg fixture consists of a fixation frame which is pivotably mounted relative to the stand 3 and, thus, also to the operating table 1, and whose pivoting movement takes place about a pivot hinge 13 adapted to the range of movement of the knee-joint. The pivot hinge 13 extends transverse to the longitudinal direction of the operating table and the patient. It determines the pivoting movement of the leg fixture, which movement takes place in the sagittal plane of the leg. In this way the lower leg 12 of the patient can be swung in a defined plane relative to a fixed reference axis. The pivot hinge is placed at such a height and is supported by two brackets 14 on the stand in such a way that the thigh 15 of the patient is held essentially horizontal. The angle of the femur relative to a horizontal axis can suitably be set by means of a height-adjusting mechanism (not shown) for the trunk fixture 4. The fixation frame essentially consists of two guide bars 16 which run parallel to each other at such a distance that the lower leg 12 of the patient is accommodated between these with a necessary margin for lateral movement. The leg fixture 11 has three fixation members 17, 18, 19, namely a first fixation member 17 for fixing the knee-joint part 20 belonging to the femur 66, a second fixation member 18 for fixing the upper end of the tibia 21 and, thus, the knee-joint part 22 belonging to the tibia, and a third fixation member 19 for fixing the lower end 23 of the lower leg, i.e. essentially the ankle. The first two fixation members 17, 18 expediently consist of rod elements which are either driven completely through the bone tissue or are driven in to bear against the femur or tibia. These two fixation members 17, 18 are adjustably fixed on the fixation frame 11 by means of displaceable runner members 24, 25 in the form of, for example, sleeve-shaped elements which can be moved along the guide bars and which can be locked, by means of locking members, at selected positions along the guide bars. The runner members have transverse openings through which the rod elements extend. The third fixation member has an element, for example in the form of a rod 26, extending between the guide bars in conformity with the direction of the rod elements, which rod 26 is likewise supported by two runner members 27, of the same type as support the first two fixation members, and can be locked in a corresponding manner. The transverse element 26 has a holder element which constitutes the fixation member and which is padded to bear against the ankle. The element is advantageously adjustable in such a way that it can be adapted to different sizes of ankle, or alternatively the holder element is designed to permit secure positional holding regardless of the dimensions of the ankle. As indicated by the two-way arrow 28, the position of the lower part of the tibia can be adjusted sideways by means of a lockable adjustment device, which can comprise a locking arrangement known per se for the transverse element 26, which can be moved sideways in the associated runner members 27.

The fixation instrument 11 also includes a stretching device 29 (tensor), an example of whose construction is shown in FIG. 2. The stretching device is designed as a tensile screw 30 for each guide bar 16, which bars are axially displaceable in a mounting 31 which is connected to the pivot hinge 13. The tensile screw 30 is threaded in the mounting and is displaced axially relative to this by means of screwing and thus acts on the end of the associated guide bar 16. Thus, by means of the stretching device 29, the tibia 21 can be stretched in order thereby to separate the parts of the knee-joint, as is necessary in surgery of the knee-joint.

As a result of its pivotability about the hinge 13, the fixation frame 11 and, thus, the tibia 21 can be set in different angular positions relative to the main plane of the operating table 1, i.e. the normal horizontal plane and the frontal plane of the patient. The tibia can thus be swung in the sagittal plane of the leg. The fixation frame 11 can be locked in the chosen angular position by means of a locking device on the pivot hinge 13 which, in the simplest case, can be made up of a locking pin which locks through locking holes 32 situated opposite each other in the mounting 31 and the bracket 14, in which respect, for example, the bracket has a number of alternative holes for different angular positions. Alternatively, the locking device can consist of a mechanism known per se for frictional locking, where secure clamping on the axle of the pivot hinge is effected, for example, by a locking screw. This can be supplemented by angle-reading (not shown), for example a graduated arc for confirming the correct angular position The important positions for knee-joint replacement are essentially the position in which the leg is straight according to FIG. 1, and in which the leg is bent according to FIG. 2. In the position according to FIG. 1, i.e. with the fixation frame 11 and the tibia 21 horizontal, the knee-joint 20, 22 is fixed by means of alignment of the limb 12 which is to be treated. This fixation is carried out in order to achieve a well-defined, fixed position of the tibia 21 and femur 66 with respect to each other and relative to the stand 3, which defines a reference position in space so that a correct surgical intervention can be performed with accurate cutting and with correct assembly of the joint prosthesis. The kneejoint parts 20, 22 of the femur 66 and tibia 21 are thus fixed by means of fixation members 17, 18, and the lower end 23 of the tibia is fixed in the third fixation member 19, and the trunk is fixed in its support device 4 by tightening and locking the hip-positioning members 9 against the hip-bones. Thereafter, the femur 66 is aligned relative to the tibia 21 by means of lateral displacement of the trunk, which is achieved by moving the slide 5 of the support device 4. This is expediently carried out with x-ray screening of the limb and checking that the desired geometry has been achieved. For example, in a normal case, it is desirable for the centre of the knee-joint parts 20, 22 to be in a straight line between the centre of the hip-joint 33 and the centre of the ankle-joint. The said alignment is carried out by fixing the tibia and moving the femur 66 by means of lateral displacement of the trunk of the patient, which is achieved by moving the support device 4 on the guide device 6 and locking it in the selected position. A lesser lateral adjustment can also be obtained by moving the lower end 23 of the tibia sideways by means of the fixation member 19 being laterally displaced and locked in the chosen position As has been mentioned above, the trunk can also advantageously be moved vertically by raising and lowering the support device 4 by means of a mechanism which can vary the vertical distance of the support device from the guide device 6.

The arrangement according to the invention comprises, in addition to the alignment instrument 2, cutting equipments for surgical treatment of the knee-joint. Certain types of knee-joint prostheses have anchoring elements intended to be anchored in the knee-joint parts of the femur or tibia from the side. For this purpose, a cutting and assembly tool 34 is incorporated in the arrangement according to the invention, which tool is shown in FIG. 3 mounted on the alignment instrument 2 and, more specifically, on the two guide bars 16 of the fixation frame 11. An example of the cutting instrument 34 is shown on a larger scale in FIGS. 4 and 5, from which it emerges that the instrument is supported on a bracket 35 which is designed as a slide, displaceable along the guide bars 16 and lockable in the desired displacement position by means of a locking device 36, for example by means of frictional locking. This is achieved, for example, by means of securing sleeve-shaped parts 37 around the guide bars. The cutting tool consists of a rotating, for example electrically or pneumatically driven, machine 38 which rotates a drill 39 or a cutter in order to produce a channel in the bone tissue for the anchoring element. The rotating machine 38 is supported by a tool holder 40 designed to set the cutting tool in the desired position both vertically and horizontally. This is achieved by means of setting mechanisms for both the vertical and horizontal directions. In the example shown, these consist of a vertical shaft 41 and a horizontal shaft 42 which are threaded and can be rotated by means of rotating wheels 43, 44. The holder 40 has a part 45 which can be moved vertically by means of the screw shaft 41 and which in turn has a part 46 which can be moved horizontally by means of the screw shaft 42 and which in turn supports the rotating machine. In connection with the displaceability along the fixation frame of the alignment instrument, a complete adjustability of the cutting tool in the vicinity of the knee-joint is thus obtained in three coordinate axes at right angles to each other. The cutting is preceded by a precise setting of the tool to the correct position in front of the cutting site. Thereafter, the tool is put into operation and is moved successively along the shaft 42 to a chosen position, which is read off on a length scale.

The arrangement according to the invention also includes a positional control unit 47 for a measuring and cutting instrument 48. This instrument is intended to produce with high precision, in the knee-joint parts of both the femur and tibia, an atraumatic cutting of the bone tissue in order to permit osseointegration with the joint prosthesis. This positional control unit 47 consists of an additional frame which is arranged on specially provided attachment devices 49 on the stand 3. In the example shown, these consist of four sleeve-shaped units which are arranged securely on the stand and in each case have a locking device 50 for locking the positional control unit, which has four legs intended to be moved down and locked in the attachment device by means of, for example, locking screws or locking pins. The positional control unit 47 is intended to be arranged with the fixation frame 11 of the alignment instrument swung down, and is made up of three sets of guide arrangements 51, 52, 53 which extend at right angles to each other and are supported by a stand 54, which is secured in the attachment devices 49. The three guide arrangements are directed at right angles to each other along three coordinate axes at right angles to each other in order to permit, within a necessary range, the adjustment of the measuring and cutting tool 48 in each desired position in space. The measuring and cutting tool 48 is in reality two separate tools, which can be arranged exchangeably on the slide 57 so as to be used in two separate moments, the measuring tool being used during a measuring moment and the cutting tool being used during a cutting moment. The measuring tool consists of a conventional measuring probe with associated surrounding equipment and is arranged on the slide 57. Exact measurement of the surface geometry of the knee-joint and, thus, its condition gives the value for its subsequent cutting. The cutting tool consists of a rotating machine 59 in the form of a drill with variable speed. The slide 55 and, thus, also the remaining slides 56, 57 are roughly adjusted as regards the displacement in the horizontal plane, i.e. in the direction to or from the knee-joint of the patient. This is achieved by means of a manual displacement of the slide and a locking in a suitable starting position by means of a locking device 60. The displacement movement for the other slides relative to the first slide is achieved by means of separate adjusting mechanisms 61, 62, 63 which, in the example shown, consist of screw axes which are rotated by means of manoeuvering knobs 64. The slide 56 can moreover be locked by means of a locking device 65.

The positional control unit 47 described above allows for cutting with high precision, in which respect tools can be set with great precision in predetermined positions relative to the knee-joint. Plane and also perpendicular cutting surfaces are obtained simply by virtue of the fact that the cutting tool can be moved in one plane at a time.

The above description has not dealt with the moments which relate to assembly of the anchoring element or prosthesis parts, the sequence of which depends on the actual procedure. The assembly of the anchoring elements can, for example, be effected by using the associated cutting tools. The remaining assembly can be effected with the positional control unit 47 removed, but expediently with the leg still aligned by means of the alignment instrument.

The invention is not limited to the exemplary embodiment described above and shown in the drawings, but can be varied within the scope of the subsequent patent claims. For example, when using anchoring elements directed from the front, the cutting tool shown in FIGS. 3, 4 and 5 can be omitted and replaced by the cutting tool shown in FIGS. 6, 7 and 8. Moreover, the positional control unit 47 can be designed in a number of different ways in order to permit a positional control of the cutting tool in space. Both the cutting tools can, for example, be designed to be turned and, thus, set at an angle relative to the horizontal plane and/or vertical plane in order to permit an angled positioning of the anchoring elements or inclined cutting surfaces.

We claim:

1. Arrangement for fixing a knee-joint in defined positions and for positional control of instruments for replacing the knee-joint of a patient with a prosthesis, which arrangement is designed to be connected to an operating table (1) intended to support the patient, characterized in that the arrangement comprises, on the one hand, a stand (3) which can be connected to the operating table (1), an alignment instrument (2) which is supported by the stand and is used for aligning both femur and the tibia relative to a reference axis, and, on the other hand, a positional control unit (47) which can be connected to the stand in defined positions and is used for positional control of at least one instrument (48) relative to the knee-joint, which alignment instrument comprises a fixture (4), supported by the stand, for the trunk of the patient, which trunk fixture is adjustable and can be locked in selected positions by displacement transverse to the said reference axis, and a limb fixture, supported by the stand, for fixing the knee-joint (20, 22) and ankle-joint (23) of the patient, in that the said limb fixture (11) for fixing the knee-joint and ankle-joint consists of a fixation frame which is pivotably mounted on the stand by means of a pivot hinge (13) and which, by means of its pivotability, can be set in different angular positions relative to the operating table.

2. Arrangement according to patent claim 1, characterized in that the trunk fixture (4) consists of a lockable slide (5) which is displaceable between different positions relative to the said reference axis and transverse to it, with a fixation arrangement (9) for the trunk.

3. Arrangement according to patent claim 1, characterized in that the limb fixture has fixation members (17, 18) for fixing, on the one hand, the knee-joint in connection with the pivot hinge and, on the other hand, a fixation member (19) for fixing the ankle-joint in the fixation frame.

4. Arrangement according to patent claim 1, characterized in that the said fixation members consist of a first fixation member (17) for fixing the knee-joint part (20) belonging to the femur (66), a second fixation member (18) for fixing the knee-joint part belonging to the tibia (21) in the fixation frame (11), and a third fixation member (19) for fixing the ankle-joint in the fixation frame.

5. Arrangement according to patent claim 4, characterized in that the first fixation member (17) is supported by the pivot hinge and the two other fixation members (18, 19) are supported by the fixation frame, and a stretching device (29) is also included, by means of which the distance between the first fixation member and the two other fixation members can be adjusted.

6. Arrangement according to patent claim 1, characterized in that the positional control unit (47) consists of an additional part designed to be releasably fixed on the stand (3).

7. Arrangement according to patent claim 1, characterized in that the positional control unit (47) is designed to support a cutting instrument (59).

8. Arrangement according to patent claim 1, characterized in that the arrangement comprises a second positional control unit (34), which is supported by the fixation frame and can be set in different positions along the latter.

9. Arrangement according to patent claim 8, characterized in that the said second positional control unit (34) is designed to support a second cutting instrument.

* * * * *